United States Patent [19]

Hammerslag et al.

[11] Patent Number: 5,108,368
[45] Date of Patent: Apr. 28, 1992

[54] STEERABLE MEDICAL DEVICE

[75] Inventors: Julius G. Hammerslag, San Juan Capistrano; Gary R. Hammerslag, Dana Point, both of Calif.

[73] Assignee: Pilot Cardiovascular System, Inc., San Clemente, Calif.

[21] Appl. No.: 583,819

[22] Filed: Sep. 17, 1990

Related U.S. Application Data

[63] Continuation-in-part of Ser. No. 461,049, Jan. 4, 1990, Pat. No. 4,998,916, which is a continuation of Ser. No. 295,124, Jan. 9, 1989, Pat. No. 4,921,482.

[51] Int. Cl.⁵ ............................................. A61M 37/00
[52] U.S. Cl. ..................................... 604/95; 604/280; 128/772
[58] Field of Search ................. 604/95, 164, 170, 194, 604/227, 280–283; 128/657, 756, 757, 772

[56] References Cited

U.S. PATENT DOCUMENTS

| | | |
|---|---|---|
| Re. 33,166 | 2/1990 | Samson .................... 606/194 |
| 3,470,876 | 10/1969 | Barchilon ................ 128/772 |
| 3,547,103 | 12/1970 | Cook ........................ 128/772 |
| 3,605,725 | 9/1971 | Bentov .................... 128/772 |
| 3,625,200 | 12/1971 | Muller. |
| 3,757,768 | 9/1973 | Kline ....................... 128/772 |
| 3,773,034 | 11/1973 | Burns et al. ............ 128/772 |
| 4,456,017 | 6/1984 | Miles ................... 604/227 X |
| 4,538,622 | 9/1985 | Samson et al. ....... 604/170 X |
| 4,543,090 | 9/1985 | McCoy ...................... 604/95 |
| 4,545,390 | 10/1985 | Leary ...................... 128/772 |
| 4,554,929 | 11/1985 | Samson et al. . |
| 4,581,017 | 4/1986 | Sabota . |
| 4,582,181 | 4/1986 | Samson . |
| 4,616,653 | 10/1986 | Samson et al. . |
| 4,641,654 | 2/1987 | Samson et al. . |
| 4,650,466 | 3/1987 | Luther . |
| 4,654,024 | 3/1987 | Crittenden et al. . |
| 4,719,924 | 1/1988 | Crittenden et al. . |
| 4,721,117 | 1/1988 | Mar et al. . |
| 4,723,936 | 2/1988 | Buchbinder et al. . |
| 4,724,846 | 2/1988 | Evans, III . |
| 4,726,369 | 2/1988 | Mar . |
| 4,748,981 | 6/1988 | Crittenden . |
| 4,748,982 | 6/1988 | Horzewaki et al. . |
| 4,757,827 | 7/1988 | Buchbinder et al. . |
| 4,758,222 | 7/1988 | McCoy . |
| 4,763,647 | 8/1988 | Gambale . |
| 4,766,249 | 8/1988 | Arenas et al. . |
| 4,775,371 | 10/1988 | Mueller, Jr. . |
| 4,798,598 | 1/1989 | Bonello et al. . |
| 4,813,434 | 3/1989 | Buchbinder et al. . |
| 4,815,478 | 3/1989 | Buchbinder et al. . |
| 4,820,349 | 4/1989 | Saab . |
| 4,827,941 | 5/1989 | Taylor et al. . |
| 4,832,047 | 5/1989 | Sepetka et al. . |
| 4,846,186 | 7/1989 | Box et al. . |
| 4,846,193 | 7/1989 | Tremulis et al. . |
| 4,850,351 | 7/1989 | Herman et al. . |
| 4,875,481 | 10/1989 | Higgins . |
| 4,875,489 | 10/1989 | Messner et al. . |
| 4,877,031 | 10/1989 | Conway et al. . |
| 4,886,067 | 12/1989 | Palermo . |
| 4,892,519 | 1/1990 | Songer et al. . |

FOREIGN PATENT DOCUMENTS 193885  1/1965  Sweden .

Primary Examiner—John D. Yasko
Attorney, Agent, or Firm—Knobbe Martens Olson & Bear

[57] ABSTRACT

An elongate steerable implement is disclosed, which may be either a steerable guidewire or catheter for coronary angioplasty applications. A floppy steerable tip on a steering region at the distal end of the implement and a control device at the proximal end are connected by means of a plurality of axially movable deflection wires extending throughout the implement. Manipulation of the control permits deflection of the steering region throughout a full 360° range of motion about the axis of the implement, without axial rotation or "torquing" thereof. In another embodiment, a steering ribbon is disclosed which permits steering by lateral deflection of the tip into a deflected or bent position and then permits straightening the tip back to its original position.

21 Claims, 5 Drawing Sheets

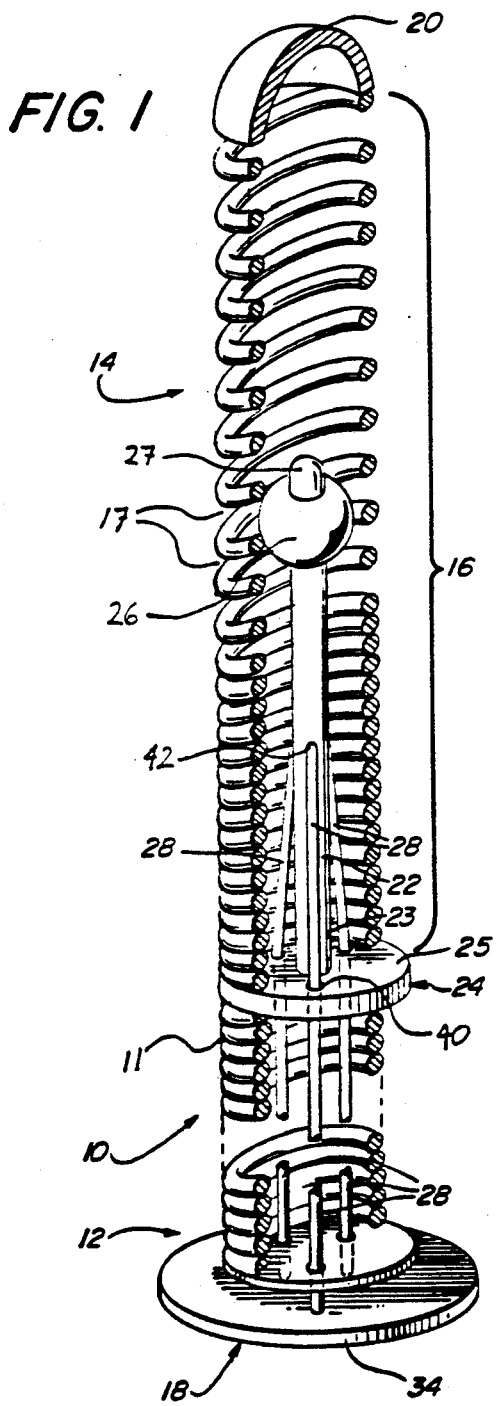
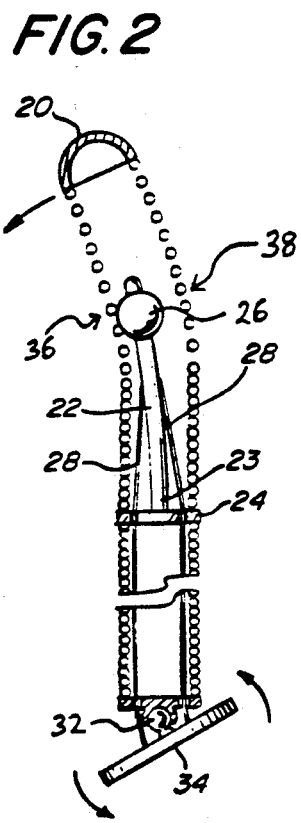
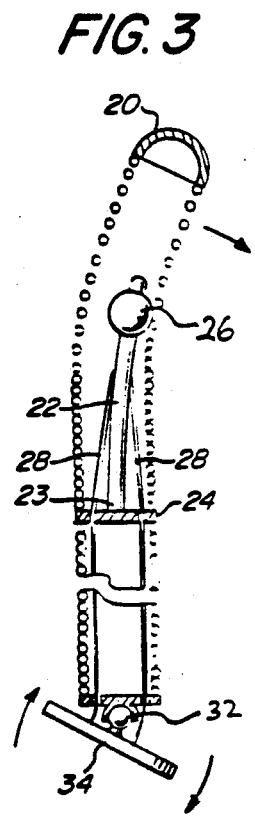
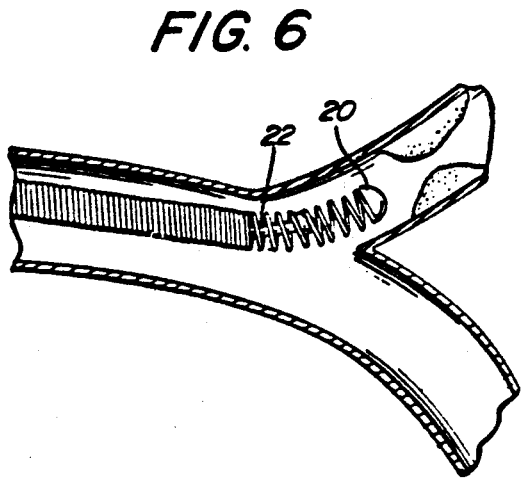

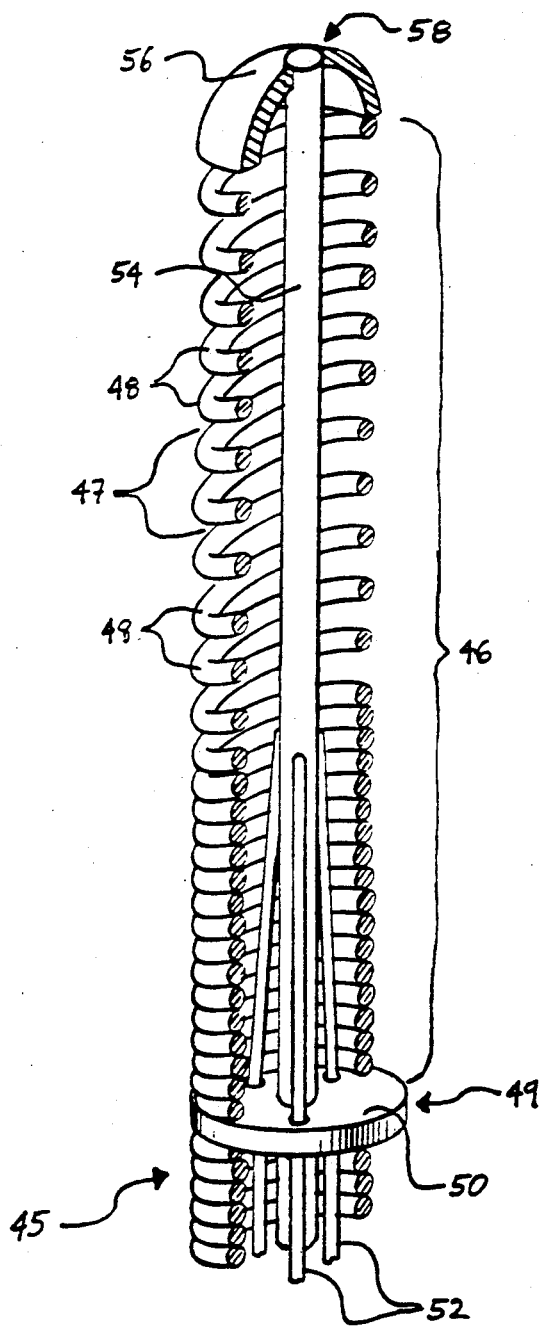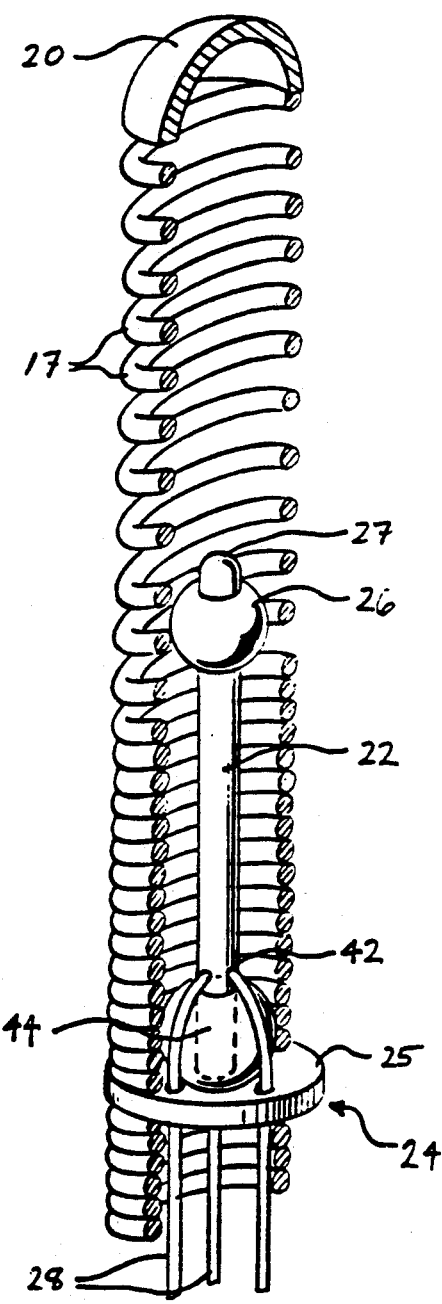

STEERABLE MEDICAL DEVICE

BACKGROUND OF THE INVENTION

This is a continuation-in-part of U.S. patent application Ser. No. 461,049, filed Jan. 4, 1990, now issued as U.S. Pat. No. 4,998,916 inventors Julius G. Hammerslag and Gary R. Hammerslag, entitled "Steerable Medical Device;" which is a continuation-in-part of parent U.S. patent application Ser. No. 295,124, filed Jan. 9, 1989; now U.S. Pat. No. 4,921,482 inventors Julius G. Hammerslag and Gary R. Hammerslag, entitled "Steerable Angioplasty Device."

The present invention relates to steering devices such as may be used with catheters, cannulae, guidewires and the like. More particularly, the present invention relates to catheters and guidewires that are steerable through body lumen or cavities and positionable within or aimable at obstructions, organs or tissue within the body from a position external to the body.

Medical catheters generally comprise elongate tubelike members which may be inserted into the body, either percutaneously or via a body orifice, for any of a wide variety of diagnostic and therapeutic purposes. Such medical applications frequently require use of a catheter having the ability to negotiate twists and turns, particularly with regard to certain cardiovascular applications.

One such application, "Percutaneous Transluminal Coronary Angioplasty" (balloon angioplasty), requires manipulation of a catheter from a position outside the patient's body through extended portions of the patient's arterial system to the stenotic site for the purpose of alleviating the obstruction by inflating a balloon. This particular procedure has been performed with increasing frequency over the past years in preference to open heart bypass surgery, when possible.

In a typical angioplasty procedure, a guidewire is transluminally inserted into the brachial or the femoral artery, to be positioned within the stenotic region and followed by a balloon catheter. The cardiologist usually pre-bends the distal tip of the guidewire before insertion and then rotates (or torques) the wire once it has reached a branch artery to enable the guidewire to enter the branch. If the angle of the bend has to be adjusted, the guidewire must be removed, re-bent and reinserted, sometimes several times. Particular difficulty is encountered with prebending where an artery branches at one angle, and then sub-branches at a different angle. This procedure is attended by the risk of significant trauma to the arterial lining, and, in many cases, the obstruction cannot be reached at all with the guidewire and catheter.

Coronary arteries are tortuous, have many sub-branches and often the obstruction is either located where the diameter of the artery is small or, by its very presence, the obstruction leaves only a very small opening through which a guidewire and/or catheter can be passed. Consequently, the cardiologist often finds it very difficult to maneuver the guidewire or catheter, which are typically several feet long, from the proximal end.

Steering the pre-bent guidewire is further complicated by the fact that branches project at all different radial angles, thus necessitating rotation of the guidewire to the appropriate degree to enter the desired arterial branch. However, rotation of the distal end of the wire typically lags behind rotation of the proximal, control end, so that precise rotational control is not possible. Also, friction in the arteries can cause the distal end to rotate in a jerky fashion which can traumatize the vascular intima.

In another application, Transluminal Laser Catheter Angioplasty (laser angioplasty), the delivery of laser energy from an external source to an intraluminal site to remove plaque or thrombus obstructions in vessels is accomplished by providing a waveguide such as a fiber optic bundle within a catheter. The nature of laser angioplasty requires an even greater ability to precisely manipulate the catheter, to control and aim the laser light at the specific plaques or thrombi to be removed.

A variety of attempts have been made in the past to provide catheters which are steerable from the proximal end to enable the catheter to be aimed or advanced through non-linear body cavities. For example, U.S. Pat. No. 4,723,936 to Buchbinder, et al. discloses a balloon catheter, which is said to be steerable from the proximal end. The catheter is provided with a deflection wire going along the entire length of the catheter, which may be axially displaced to cause deflection at the distal end. However, the tip of the catheter can be bent in one direction only, and the entire catheter must be rotated or torqued to be guided. A further disadvantage of this device is the inability to effectively straighten the catheter once it has been bent. Any ability of the Buchbinder catheter depends upon the axial compression of the steering wire therein. In addition, the design requires a relatively large diameter deflection wire, which precludes extremely thin diameter catheters, such as those preferred for use for laser or balloon angioplasty applications.

U.S. Pat. No. 3,470,876 to Barchilon discloses a catheter device having a central lumen extending therethrough, and four tensioning cords extending along an inner wall of the catheter. The '876 patent specifically recites that catheters may be produced in accordance with the Barchilon design having diameters of 0.125 to 2 inches, and are suited for applications such as within the duodenal bulb or ascending colon. These diameters are unsuited for use as a guidewire in coronary angioplasty, which typically requires diameters in the area of as small as from about 0.014 to 0.018 inches.

In the context of coronary angioplasty applications, the prior art generally suffers from disadvantages such as limited steerability and excessive external diameters. Limited catheter tip steerability results in greater time spent in the body and significantly elevated risk of trauma both to the vascular intima and to the patient in general. Multiple insertions of guidewires or catheters may lead to thrombosis, as a result of coagulation commencing along a guidewire surface. Additionally, precise directional control in laser angioplasty is of the utmost importance to assure accurate aiming of the laser beam to ablate the attendant plaque. However, the only prior art catheters having multi-directional steerability are typically greatly in excess of practical angioplasty catheter diameters.

In addition to limited steerability, the prior art guidewires, such as those disclosed by Buchbinder and in U.S. Pat. No. 4,719,924 to Crittenden, rely upon the spring tension of the guidewire coil (and the resilience of the distal end of the deflection wire, in the case of Buchbinder) to return the guidewire to the straight, unbent position. However, as important as deflecting the wire to enter a branch artery is straightening the wire after the branch is negotiated. Any ability to straighten in the prior art devices described above results from the spring tension or other structure in the distal end of the wire, which structures also compromise the desired floppiness of the guidewire tip.

Thus, there remains a need for a small diameter steering device, which may be readily adapted for use in the construction of either guidewires or catheters, and which is especially suited for procedures such as balloon or laser angioplasty. Preferably, the steering device is constructed in a manner which permits a diameter as small as that of existing dilatation catheters or guidewires used in angioplasty applications, yet is capable of complete deflective movement, throughout a full 360° range of motion, without axial rotation.

SUMMARY OF THE INVENTION

In accordance with one aspect of the present invention, there is provided an improved steerable guidewire or catheter implement of the type useful for percutaneous transluminal insertion into the coronary vascular system. The invention permits controlled negotiation of branches and turns to guide an angioplasty catheter or guidewire to an arterial stenosis or lesion or other treatment site without the need for prebending or torquing of the instrument. The distal tip on steerable implements made in accordance with one embodiment of the present invention can be controllably radially displaced in any direction, thus permitting a full 360° range of motion without the need to rotate the body of the steerable implement.

In one embodiment of the present invention, a guidewire is provided having an elongate flexible shaft with a central lumen extending therethrough and a floppy resilient tip on the distal end. An axially extending steering post is disposed within a steering region on the distal portion of the flexible shaft. The steering post is pivotably secured at its proximal end to a radial support axially secured within the flexible shaft at the proximal end of the steering region, to prevent axial displacement of the steering post while at the same time permitting lateral deflection of the steering post out of parallel with the axis of the flexible shaft.

At least one and preferably two or three or four deflection wires are axially movably disposed within the lumen of the flexible shaft, and extend proximally from a distal point of attachment on the steering post throughout the length of the flexible shaft to a control at the proximal end thereof. Each deflection wire passes through a notch or orifice on the radial support.

In another embodiment, the steering post is provided with a wire anchor region at its distal end and a wire guide region at its proximal end. Preferably, the cross-sectional area of the post at a point intermediate the anchor region and guide region is less than the cross-sectional area of the post at least one of the anchor region and guide region, and, more preferably, is less than the cross-sectional area of the post at both the guide region and anchor region.

In a further embodiment, a deflection wire anchor is disposed in the steering region of the flexible shaft, spaced apart in a distal direction from a deflection wire guide. Preferably, opposing pairs of deflection wires are formed by providing a continuous length of wire which loops at its midpoint across the distal end of the anchor, both ends extending through the flexible shaft in a proximal direction.

Axial movement of any one of the deflection wires in a proximal direction displaces the axis of the steering post in a unique lateral direction, and through combinations of proximal axial displacement of more than two deflection wires, the steering post is caused to deflect laterally and rotate throughout a full 360° range of motion about the axis of the flexible shaft. In a two wire embodiment, the deflection wires are preferably disposed in parallel to and on opposite sides of the longitudinal axis of the device to permit bending the tip by pulling on one wire and straightening the tip by pulling on the other wire.

The steerable medical device of the present invention can thus negotiate tortuous and branched arterial systems, without the need for withdrawal and multiple insertions to deflect the tip, or axial rotation of the catheter body. The steerable medical device can be readily manufactured in accordance with known techniques, and at a low per unit cost.

These and other features and advantages of the present invention will become apparent from the detailed description of preferred embodiments which follows, when considered together with the attached drawings and claims.

BRIEF DESCRIPTION OF THE DRAWINGS

FIG. 1 is a partial sectional perspective view of a steerable guidewire according to the present invention, with the outer tubular casing removed.

FIG. 2 is an elevational sectional view of the guidewire of FIG. 1, illustrated in a first deflected position.

FIG. 3 is an elevational sectional view of the guidewire of FIG. 1, illustrated in a second deflected position.

FIG. 4 is a partial sectional perspective view of a steerable laser angioplasty catheter according to the present invention.

FIG. 5 is a further embodiment of the steerable guidewire of the present invention.

FIG. 6 is a schematic view of the guidewire of FIG. 1, illustrated as negotiating an arterial branch point and approaching an arterial stenosis.

DETAILED DESCRIPTION OF PREFERRED EMBODIMENTS

Figure 7:
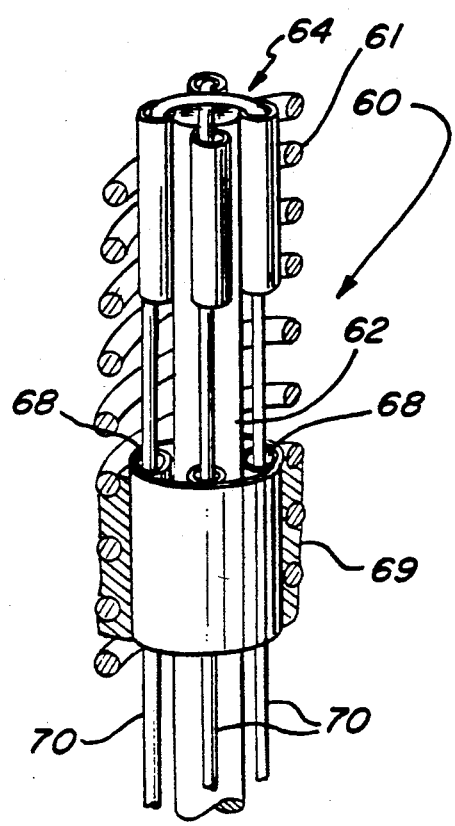
FIG. 7 is an elevational perspective view of a further embodiment of a steering device according to the present invention.

Referring to FIG. 1, there is disclosed an elongate flexible implement 10, having a tubular body 11 with a proximal end 12 and a distal end 14. The distal end 14 comprises a steering region 16, and the proximal end 12 is provided with a control 18 for steering the implement 10, which may be, for example, a steerable guidewire or catheter. Although the steering device of the present invention will generally be described herein as incorporated into an angioplasty guidewire, it is to be understood that one skilled in the art will be able to readily adapt the steering device to other medical and non-medical applications.

The body 11 of steerable implement 10 may be any desired length from inches to many feet depending upon the intended application. In an embodiment useful as an angioplasty guidewire or catheter, the body 11 will typically be several feet long, and will preferably be about 135-180 cm, as is typical of existing angioplasty catheters and guidewires respectively. However, any suitable length may be used.

The body 11 may be constructed in any of a variety of ways known in the art, such as by tightly winding a coil of metal wire, or extrusion of a relatively flexible biocompatible polymer such as polyethylene. Wound guidewires preferably comprise a high tensile strength wire of a resilient, non-corrosive metal such as stainless steel or platinum, and may have a circular cross-section with a diameter of from about 0.001 to 0.020 in. The wire may alternatively have a rectangular cross-section of from about 0.001 to 0.020 inches by from about 0.001 to 0.040 inches, or other variations known in the art. Construction materials and techniques for manufacturing wire wound guidewires are well known in the art, and a typical 180 cm teflon coated 0.014 inch or 0.016 inch diameter non-steerable guidewire may be obtained from U.S. Catheter, Inc., a division of C.R. Bard, Inc., located in Billerica, Mass. U.S.A.

The external diameter of wire wound guidewires will of course be a function of the intended application. The wire wound coronary angioplasty guidewires incorporating the steering device of the present invention are preferably wound to have an external diameter in the range of from about 0.014 inches to about 0.018 inches. In steerable catheter applications, the diameter of the catheter can be varied to optimize the diameter of a central working channel as desired, while still maintaining a sufficiently small exterior diameter for the intended application. Steerable balloon angioplasty catheters incorporating the present invention will typically have an exterior diameter in the range of from about 0.020 inches to about 0.041 inches or larger as permitted by location of the lesion.

Preferably, the exterior surface of the wound coil type guidewire shaft 10 is provided with an elastic, biocompatible coating or sheath to provide a smooth outer surface. Suitable coatings can be formed by dipping, spraying or wrapping and heat curing operations as are known in the art. Alternatively, heat shrinkable tubing can provide a suitable outer sheath. A coating material should be selected which will permit sufficient flexing of the body 11 without cracking, will minimize sliding friction of the implement 10 during insertion and removal, and is substantially chemically inert in the in vivo vascular environment. A variety of suitable materials are known, including, for example, polytetrafluoroethylene, urethane or polyethylene.

The body 11 of flexible implement 10 typically terminates at its distal end 14 in a closed tip 20. Numerous guidewire and catheter tip constructions are known in the art and need not be detailed extensively herein. In general, the tip 20 is preferably a rounded closure constructed of a resilient polymeric material such as silicone or urethane which will minimize trauma to the vascular intima, as will be appreciated by one of skill in the art. As a safety feature, to facilitate complete removal of fragments of a broken guidewire, a safety wire may be secured at one end to the inside of the tip 20, and at the other end to the post 22 or support 24.

Disposed intermediate the tip 20 and body 11 of a flexible implement 10 in accordance with the present invention is a floppy but controllable steering region 16. Steering region 16 is constructed in a manner that facilitates lateral displacement of the tip 20 relative to the axis of the body 11, through physical design and/or choice of flexible construction materials.

For example, in a typical angioplasty guidewire or catheter, where the flexible body 11 comprises a metal wire coil, the revolutions of wire per unit of axial distance along the body is reduced in the steering region 16 relative to body 11 to provide a looser wound coil having space 17 between adjacent wire loops, as illustrated in FIGS. 1-6. Thus, referring to FIG. 2, it can be seen that lateral deflection of steering region 16 to the left may involve both an axial compression of adjacent wire loops on the inside surface 36 of the bend, and an axial separation of the adjacent wire loops on the outside surface 38 of the bend.

Alternative designs or materials can be employed, provided that the catheter exhibits sufficient lateral flexibility. In general, the steering region 16 may be made from a variety of suitable metal or plastic coils or flexible sleeves. Materials opaque to X-rays, such as platinum, gold, tungsten, tantalum or the like, may be advantageously incorporated therein, to act as a fluoroscopic marker to aid in visualization.

In accordance with the steering mechanism of the present invention, a steering post 22 is provided, extending in a generally axial direction within the steering region 16 of flexible body 11. Preferably, the steering post 22 is disposed coaxially within the central lumen of steering region 16 when the steering region 16 and body 11 are linearly aligned, such as when at rest. See FIG. 1. As will be described, the steering post 22 is secured in the steering region 16 in a manner that substantially prevents axial displacement thereof yet permits lateral deflection of the axis of the steering post 22 away from the axis of body 11.

Post 22 preferably comprises a resilient shaft which may be molded or extruded from any of a variety of materials, such as nylon, and may have a cross-sectional dimension of from about 0.002 inches up to about 0.012 inches for use in a typical steerable angioplasty guidewire embodiment. Alternatively, a variety of resilient or springy metals in the form of wire can also be used to form post 22, such as phosphor bronze or other resilient metal. In general, it is desirable to select a material which will permit some degree of bending and return to its original shape, and will resist axial compression under the forces typically applied in the intended use of the steerable implement 10.

The length of steering post 22 will, of course, be dependant upon the length of the steering region 16. In a typical steerable guidewire for angioplasty applications, the entire steering region 16 will be on the order of from about 0.040 to about 1.0 inches and preferably from about 0.120 to about 0.150 inches long, and the steering post 22 may be from one-quarter to two-thirds that length. Although steering post 22 may extend distally all the way to the distal tip 20 of the steerable implement 10, it is preferred to limit the length to the proximal one-half or one-third of the axial length of steering region 16 to minimize rigidity in the steering region 16 yet permit sufficient steerability thereof.

For example, in a typical angioplasty guidewire the distal end 27 of steering post 22 will be spaced apart from the interior surface of tip 20 by a distance of from about one-tenth to one-half an inch or more, thus permitting the steering region 16 of the catheter shaft to be as floppy as desired. However, in an embodiment where the distal portion of a fiber optics bundle or flexible tube for defining a working channel additionally functions as the steering post 22, the post 22 will extend all the way to the distal tip 20 and be exposed to the outside by way of an opening therethrough. See, for example, FIG. 4.

In a particularly preferred embodiment, steering post 22 is further provided with a bead or enlarged region 26 to optimize transmission of lateral force from the steering post 22 to the wall of steering region 16. For this purpose, bead 26 is most effectively located at or near the distal end of steering post 22. Bead 26 may be formed by dipping or coating techniques, or may be a preformed member having an opening therein for sliding over the end of steering post 22. Alternatively, post 22 can be molded or milled to provide a bead 26 integrally formed thereon. Bead 26 is preferably substantially circular in a cross-section perpendicular to the axis of post 22, and the external diameter of the bead 26 is only slightly less than the interior diameter of the steering region 16 so that maximum lateral motion of the steering post 22 is transmitted to the steering region 16, but bead 26 also remains only in slidable contact with the interior surface thereof.

The proximal end 23 of the steering post 22 is mounted to or in pivotable contact with a radial support 24, in a manner which permits pivoting of the steering post 22 throughout a full 360° range of motion about the axis of body 11. The post may also be molded or milled as an integral part of disk 24. The support 24 comprises any means by which the deflection wires 28 are displaced radially outwardly from the axis of the tubular body 11, such as by the thickness of the post 22 or other structure including the plate embodiment illustrated in FIGS. 1-3.

Referring to FIG. 1, the support 24 of the illustrated embodiment comprises a circular disk 25 located within the tubular body 11 of the steerable implement 10, preferably located near the distal end thereof. The disk 25 is axially secured within the tubular body 11 to provide a stationary radial support for at least one deflection wire 28, and pivotable mount for steering post 22. Disk 25 may be attached, for example, by friction fit between adjacent turns of coiled spring wire. Steering post 22 preferably is attached to or in contact with the disk 25 in a manner which permits it to swivel from 90 degrees to close to 0 degrees, relative to the lateral plane of disk 25.

The disk 25 may be made of stainless steel or any of a variety of other suitable materials such as other metals or plastic polymers which will provide a sufficiently axially rigid seat for the proximal end 23 of steering post 22. Disk 25 may be formed by stamping from sheet stock and drilling, injection molding, or other techniques well known in the art. Preferably, a central depression or orifice is provided thereon, for providing an axial seat for steering post 22. The diameter of disk 25 can vary, however, it will typically be no greater than, but may approximate the outside diameter of the steerable implement 10. Diameters from about 0.14 to 0.050 inches may preferably be used in the construction of cardiac angioplasty catheters.

Lateral deflection of the steering post 22 away from the axis of body 11 is accomplished by proximal axial displacement of any of a plurality of deflection wires 28 extending proximally throughout the length of flexible body 11. Although only a single deflection wire 28 or two deflection wires can be used, preferably three or four deflection wires 28 are employed to provide a full 360° range of motion of the steering region 16 about the axis of the body 11, as will become apparent. Only a single deflection wire 28 will be described in detail herein.

The distal end of deflection wire 28 is secured such as by adhesives (or brazing or soldering, etc.) to the steering post 22 at the distal end thereof, or at a variety of other locations along the length of post 22. By "attached" or "secured" to the post and similar language herein, it is to be understood that the deflection wire 28 must be mechanically linked to the post 22 but need not necessarily be directly secured thereto. For example, the deflection wire 28 could be secured to an annular flange or ring surrounding the post or other structure which may be convenient from a manufacturing standpoint to provide a sufficiently secure linkage to accomplish the intended steering function. Alternatively, an eye on the end of the deflection wire can surround the post 22 and rest against a stop formed by a milled shoulder or adhesive, or other means of attachment as will be apparent to one of skill in the art.

In one embodiment, the deflection wire 28 preferably extends radially outwardly from the point of attachment to the steering post 22 to the support 24. For this purpose, the support 24 is preferably provided with a notch or orifice 40 for each deflection wire 28 to extend through, said orifice 40 spaced radially outwardly from the axis of the tubular body 11 by a first distance. The distal end of each deflection wire 28 is secured to the steering post 22 at a point radially displaced from the axis of the steering post 22 by a second distance, and the first distance is preferably greater than the second distance to maximize the lateral component of force. The second distance preferably approaches zero; however, it will inherently include the radius of the steering post 22 where the deflection wire 28 is secured intermediate the two ends thereof.

In the most preferred embodiment of the present invention, four deflection wires 28 are provided, each passing through an orifice 40 in support 24 spaced at angles of approximately 90° apart from each other along the plane of the support 24. In a three deflection wire embodiment, as illustrated in FIG. 1, each orifice 40 is separated from each adjacent orifice by an angle of approximately 120°.

The deflection wires may be made of stainless steel, nylon or any other suitable material which provides sufficient tensile strength and flexibility. The diameter of the lines can range from 0.001 to 0.005 inches or more, and suitability of particular sizes or materials can be readily determined by experimentation.

A control device 18 for steering the catheter is shown schematically in FIGS. 1-3. The control device 18 is preferably provided at its center with a pivotable mount 32 to permit it to be tipped throughout a full 360° range of motion. In the illustrated embodiment, control 18 comprises a circular plate 34 secured to proximal end 12 of flexible shaft 10 by way of pivotable mount 32. Deflection wires 28 are spaced equally radially outwardly from the pivotable center of the control device and at equal angular distances around the plate 34. Deflecting plate 34 from a plane normal to the axis of shaft 10 transmits force via one or more deflection wires 28, a component of which is resolved into a lateral force to deflect the catheter tip toward or away from the longitudinal axis of catheter. Selective tipping of the deflection plate 34 results in rotation of the catheter tip to any desired orientation.

A variety of alternative control devices can be envisioned for use with the steerable implement of the present invention. For example, a "joy stick" type device comprising a single lever which can be displaced to any position throughout a nearly hemispherical range of motion might be used. As a further alternative, a portion of the proximal end 12 of tubular body 11 is enlarged to a cross-section of a half inch or larger to facilitate grip. The enlarged section is provided with a plurality of axially slidable switches, one corresponding to each deflection wire 28. Manipulation of the switches by the thumb or forefinger will obtain the desired deflection of steering region 16. As will be appreciated by one of skill in the art, any control device will preferably be provided with a stop to prevent bending of the post 22 or steering region 16 past its elastic limit.

A variety of factors impact the amount of the lateral force component exerted on steering post 22 by axial, proximal displacement of any of deflection wires 28. For example, as orifice 40 is moved further in a radially outward direction, the lateral force component will increase. Lateral displacement of orifice 40, however, is constrained by the maximum diameter that the steerable implement can have for an intended application.

Alternatively, shortening the axial distance from the support 24 to the point of attachment 42 of the deflection wire 28 to the steering post 22 increases the angle between the axis of post 22 and deflection wire 28, thereby increasing the lateral component of force. For this reason, support 24 is typically within one or two inches, and preferably less than one inch, from the distal tip 20 of an angioplasty catheter or guidewire embodiment of the invention.

A further alternative is illustrated in FIG. 5. In this embodiment, a fulcrum 44 is provided at a point intermediate the radial support 24 and point of attachment 42 for maintaining the deflection wire 28 concave in a radial inward direction. The fulcrum 44 may conveniently comprise a substantially radially symmetrical member such as a sphere or toroid, which can also function to limit proximal axial movement of steering post 22 through a central opening in support 24. In this embodiment, the point of attachment of deflection wires 28 may be to the fulcrum 44 instead of directly to the steering post 22.

In accordance with a further aspect of the present invention, there is provided a steerable medical implement for use in percutaneous transluminal laser angioplasty applications. Referring to FIG. 4, there is disclosed an elongate flexible implement 45 comprising at its distal end a floppy steering region 46. As described with previous embodiments, enhanced flexibility may be imparted to steering region 46 by providing spacing 47 between adjacent loops of wound wire 48.

A radial support means 49 is disposed at the proximal end of steering region 46, which may comprise a circular plate 50 or other structure for displacing deflection wires 52 radially outwardly from the axis of implement 45.

A waveguide such as a fiber optic bundle 54 extends the entire length of the implement 45, for directing laser light from a source (not illustrated) disposed at the proximal end of the implement 45, to a point of application within a coronary artery at the distal tip 56 of the implement 45. For this purpose, the optical pathway 54 extends throughout the length of steering region 46 and traverses tip 56 by way of an opening 58 therein.

Each of the deflection wires 52 is secured at its distal end to the fiber optic bundle 54 at a point intermediate radial support 49 and distal tip 56. Preferably, as has been previously described, the point of attachment of deflection wires 52 to the fiber optic bundle 54 is less than half the distance and preferably is within one-third of the distance between the radial support 49 and distal tip 56, in order to optimize the lateral component of force.

Thus, utilizing a control device as previously described, a laser angioplasty catheter incorporating the present invention permits the controlled direction of a beam of light transmitted through fiber bundle 54 at any desired point within a full 360° circle on a plane normal to the axis of the implement 45.

As is well known in the fiber optics art, numerous functions can be accomplished through a waveguide such as fiber bundle 54. For example, substantially parallel but discrete bundles of fiber optics can be secured adjacent one another within the fiber bundle 54 to permit a plurality of discrete light transmitting channels. Alternatively, a plurality of concentric optical pathways can be provided as is well known in the art.

A plurality of discrete optical pathways may advantageously be used to perform a variety of functions. For example, a first optical pathway might be utilized to permit visualization of the stenotic site or other surface to be treated. A separate optical pathway may be utilized to transmit light for illuminating the site. Yet a third optical pathway might be utilized to transmit the laser light. These and other aspects of the fiber optics and laser light source are well known to those skilled in the fiber optics art.

A variety of additional functions may be performed through use of the additional interior space within the housing of steerable implement 45. For example, in a preferred embodiment, an aspiration duct may be provided near the distal end of the implement 45, for suctioning debris or gases which may be generated as a result of the action of the laser. Alternatively, in place of a waveguide 54, a flexible tube may be incorporated into the steering device of the present invention, thereby providing a working channel to receive additional implements therethrough.

Referring to FIG. 7, there is disclosed a further embodiment of the steering device in accordance with the present invention. The steerable device illustrated in FIG. 7 can be incorporated into a guidewire, or directly into a catheter, such as a balloon dilation catheter, or other elongate implement for which steerability is desired. It is to be understood that while certain preferred dimensions and construction materials will be recited in the discussion of the present embodiment, these illustrate a single angioplasty guidewire embodiment only and in no way limit the scope of the present invention.

The steering device 60 preferably is incorporated into a steerable guidewire, of the type made from an elongate flexible tubular spring coil 61 having a central lumen extending therethrough. The spring coil 61 may be further provided with an outer sheath or coating, as are known in the art, or the spring coil may, by itself, serve as the outer wall of the guidewire. As is well known in the art, the proximal end of the spring coil 61 is made up of a plurality of adjacent loops of wire. Lateral flexibility of the spring coil 61 at a distal steering region can be enhanced by providing a spacing between adjacent loops of the spring coil. These features are illustrated in FIGS. 1-6 of a previous embodiment of the present invention, and need no further discussion here. Alternatively, the adjacent loops of wire in the steering region can be in contact with one another, i.e., no axial spacing, when the steering region is in an orientation co-linear with the axis of the adjacent guidewire.

Extending axially within the steering region of the spring coil 61 is a central post 62. Post 62 is preferably made from a flexible polymeric extrusion, although any of a wide variety of materials can be incorporated into the post 62 of the present invention. Most preferably, the post 62 comprises a nylon rod having a substantially circular cross-sectional area and a diameter of about 0.004 inches.

The distal end 64 of post 62 preferably is disposed at or near the distal end of the spring coil 61. For example, the distal end 64 in one embodiment terminates proximally of the guidewire tip (not illustrated), similarly to the embodiment illustrated in FIG. 1. Alternatively, the distal end 64 is in contact with the guidewire tip, which can be molded or machined integrally with the post 62 or secured thereto such as by known biocompatible adhesives. In either embodiment, the distal end of the spring coil 61 is provided with any of the known atraumatic tips conventional in the angioplasty arts, such as those formed by molding or dipping or brazing processes.

Most preferably, the post 62 extends in a distal direction beyond the distal ends of wire guides 72 and for a predetermined length. Provision of such a length between the distal ends of the wire guides and effective point of attachment of the pullwires causes the steering region in operation to form an "elbow" bend, which is believed clinically desirable. In addition, the portion of post 62 disposed between the end of wire guide 72 and the guidewire tip can function as a safety wire for securing the guidewire tip against in vivo detachment.

By "elbow" bend, it is meant that the bend in the guidewire occurs at a relatively discrete position displaced proximally from the distal end of the guidewire. This enables a short length of floppy guidewire at the distal end to facilitate negotiation of the artery with minimal trauma to the vascular intima.

Figure 11:
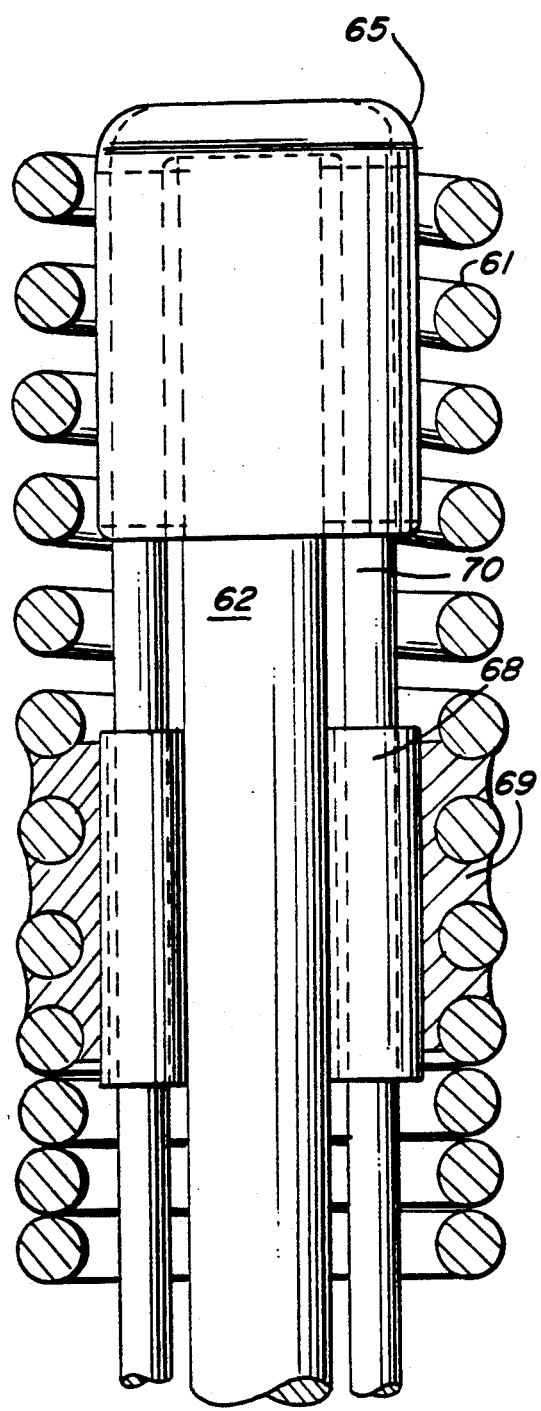
FIG. 11 is a simplified front elevational view of the device shown in FIG. 7, following application of an anchor cap.

The length of the floppy tip beyond the more rigid steering region of the guidewire can be varied, depending upon a number of considerations which will be apparent to one of skill in the art, including the diameter of the vessels expected to be traversed. In one specific construction of the embodiment of FIGS. 7 and 11, for example, the relative dimensions are as follows. Length of each of guide 68 and anchor 72: about 0.010 inches. Axial distance between guide 68 and anchor 72: about 0.006 inches. Distance between end of anchor 72 and distal tip of guidewire: about 0.140 inches. Diameter of control post 62: about 0.004 inches. Diameter of spring wire of guidewire body: about 0.002 inches. Outside diameter of assembled guidewire: about 0.014 inches.

The post 62 extends in a proximal direction through the spring coil 61 as far as may be desired for a given application, as will be understood by one of skill in the art. For example, the central post 62 may extend proximally only as far as the proximal wire guide 68, or further in a proximal direction to impart greater rigidity to the spring coil 61 than would otherwise be present.

The post 62 must at some point along its length be secured against axial movement in the proximal direction relative to the spring coil 61. From a manufacturing standpoint, it has been found convenient to secure the proximal wire guides 68 both to the post 62 and to the interior surface of spring coil 61 for this purpose as will be discussed. However, the post 62 can also be secured to the coil 61 at other locations, such as at the proximal end of an axially elongated post 62.

A plurality of proximal wire guides 68 are provided for guiding each of a plurality of deflection wires 70. Preferably, four proximal wire guides 68 are provided, equally spaced about the periphery of the central post 62. As will be apparent to one of skill in the art, three wire guides 68 spaced equidistant around the periphery of central post 62 will also allow complete 360° steerability of the guidewire. However, the use of four deflection wires 70 is preferred. Similarly, the guidewire can be constructed having only two or even a single proximal wire guide 68, with a commensurate reduction in the range of motion over which the guidewire may be steered.

A plurality of deflection wires 70 extend axially throughout the length of the spring coil 61, each through a unique proximal wire guide 68 to the distal end 64 of post 62. Preferably, the distal end 64 of post 62 is also provided with a plurality of distal wire guides 72, corresponding to each deflection wire 70.

In accordance with the preferred embodiment of the present invention, four deflection wires 70 are utilized, each deflection wire 70 having a unique proximal wire guide 68 and distal wire guide 72. Each of the deflection wires 70 may be secured to the distal end of the post in any of a variety of manners, which will be apparent to one of skill in the art, such as by mechanical anchors, adhesives or thermal or chemical welding.

Mechanical anchoring or welding of the distal end of deflection wire 70 may be difficult to accomplish while providing sufficient strength to allow repeated steering maneuvers of the steering device 60 without separation of the distal end of deflection wire 70 from the distal end 64 of post 62. Thus, although the preferred embodiment is effectively provided with four deflection wires 70, they are actually two continuous deflection wires which loop across the distal end 64 of the post 62. A first deflection wire 70 extends distally through distal wire guide 72, continuously around or over the distal end 64 of central post 62 and back proximally through the opposing wire guide 72 and continuing on towards the proximal end of the instrument. In this manner, all four ends of the two continuous wires terminate at the proximal end of the guidewire where they connect to a control device permitting selective axial reciprocating motion thereof.

Figure 8:
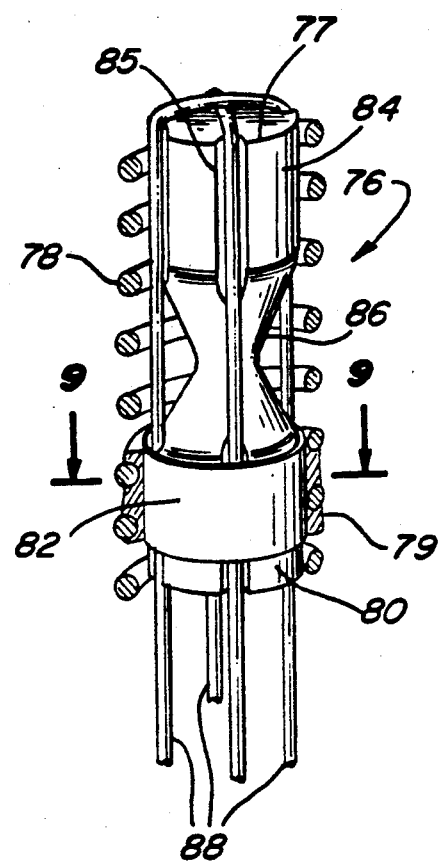
FIG. 8 is an elevational perspective view of still a further embodiment of the present invention.

In accordance with one preferred embodiment of the present invention, proximal wire guide 68 is in the form of an elongate tubular body for receiving the corresponding deflection wire 70 therethrough. The tubular wire guide 68 preferably is comprised of a material which can be readily adhered to the central post 62, and preferably also can be adhered to the adjacent loops of spring coil 61. Polyamide tubing, such as that manufactured by Polymicro Technologies, Inc. in Phoenix, Ariz., having an axial length of approximately 0.010 inches and an inside diameter of slightly greater than 0.0015 inches, preferably about 0.002 inches, has been found particularly suitable for this purpose, and can be readily adhered to a nylon post 62 using a suitable epoxy adhesive, such as that marketed under the name Ecobond by Emmerson Cuming of Canton, Mass. The length of the tube is less important than the diameter, and the diameter must be sufficient that a deflection wire extending therethrough is capable of reciprocal motion with sufficiently low friction that steering may be accomplished. The wall thickness of the tube will directly affect the minimum diameter of the assembled steerable guidewire, and is thus preferably minimized. For the polyamide tube disclosed above, the wall thickness is preferably as low as about 0.0003 inches. As illustrated in FIG. 8, the proximal wire guide 68 is conveniently affixed to the spring coil 61 by applying an epoxy 69 thereto.

Deflection wire 70 extends distally beyond the end of the proximal wire guide 68, and preferably through a distal wire guide 72. Deflection wire 70 is a fine wire of a diameter sufficient to provide enough tensile strength to allow steering of the guidewire without breaking, but small enough to permit construction of guidewires suitable for angioplasty applications. Preferably, a stainless steel wire is used, and diameters as low as about 0.0015 inches have been found functionally sufficient. However, a variety of other metals or polymers may be used, and the minimum appropriate diameter for any given material can be readily determined by one of skill in the art.

Distal wire guide 72 is in the preferred embodiment a similar construction to proximal wire guide 68. Thus, distal wire guides 72 are formed by a plurality of elongate tubular guides adhered to the central post 62 for receiving the corresponding deflection wire 70 therethrough. Alternatively, the distal wire guide 72 can simply be a groove over the distal end 64 of post 62, or a bore hole extending transversely through the center of central post 62.

Assembly of the steering device of the present invention may be accomplished in a variety of ways which will be understood by one of skill in the art, with many of the assembly steps being performed under microscopic vision. The proximal wire guide 68 and distal wire guide 72, when used, are preferably secured to the central post 62 by applying an adhesive thereto such as by dabbing with a 0.0015 inch diameter wire as an applicator. A first deflection wire 70 is threaded in a distal direction through corresponding proximal wire guide 68, through distal wire guide 72, then back in a proximal direction through the corresponding wire guides on the opposite side of post 62 and drawn through to the proximal end of the instrument. This assembly procedure is repeated for a second deflection wire. With the deflection wires 70 in place, the entire distal end 64 of post 62 is dipped in or dabbed with an epoxy or other biologically compatible material to form a cap 65 to secure each of the deflection wires 70 against axial movement relative to the control post 62. See FIG. 11.

The entire assembly of post 62 wire guides and deflection wires is thereafter inserted distal end first into the proximal end of a standard spring coil 61 and advanced until the proximal wire guide 68 is approximately axially adjacent the beginning of the distal flexible steering region on the spring coil 61. An epoxy or other biocompatible adhesive 69 is thereafter applied between the adjacent loops of spring coil 61 to secure the proximal wire guides 68 to the spring coil 61, thereby preventing axial movement of the post 62 relative to the spring coil 61. It has been found that polyamide tubing can be epoxied to the adjacent spring coil 61 using a 0.002 inch wire or other applicator tip under microscopic vision. However, care must be taken that the epoxy does not flow into contact with the deflection wire 70, in which case the deflection wire 70 would be unable to slide axially within the proximal wire guide 68.

Figure 9:
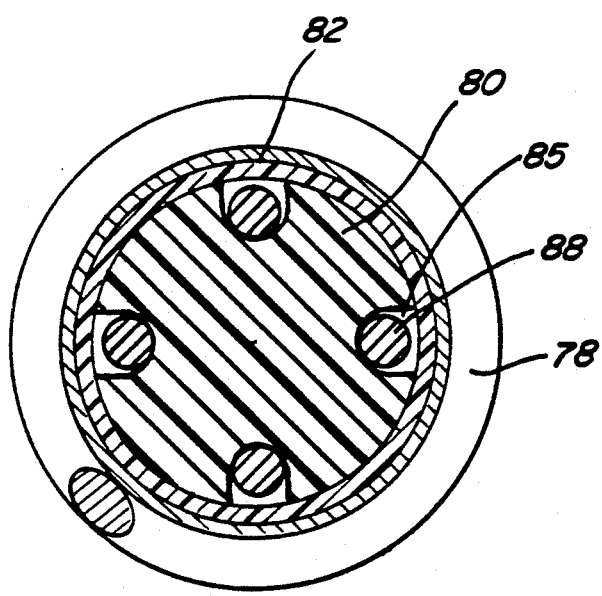
FIG. 9 is a cross-sectional view along the line 9—9 of the device of FIG. 8.
Figure 10:
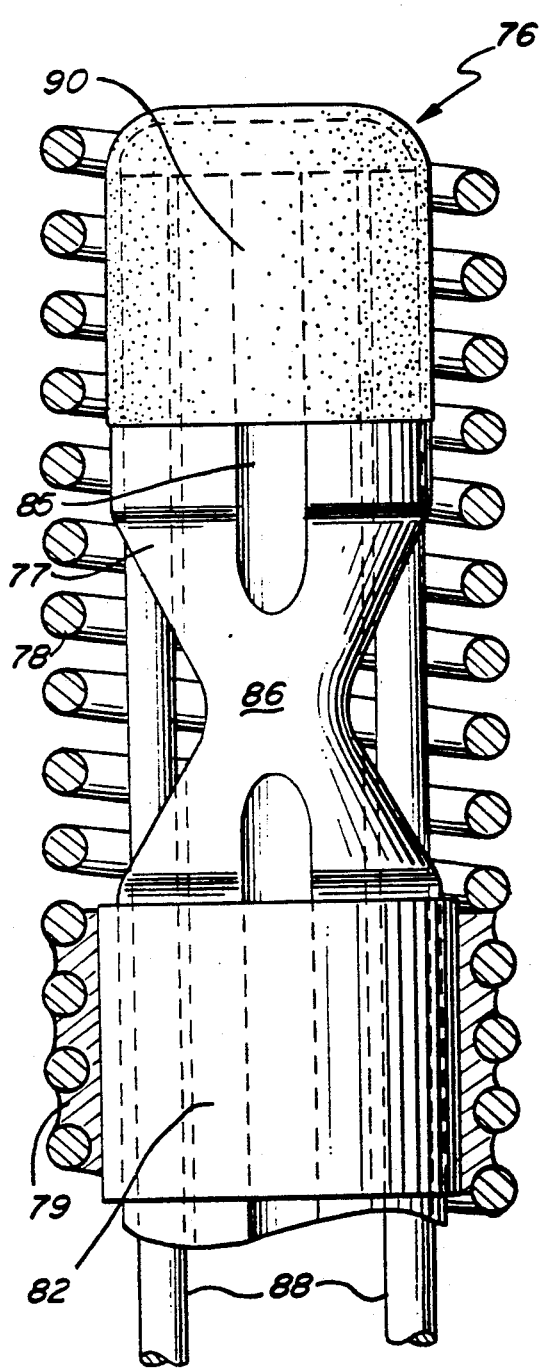
FIG. 10 is a simplified front elevational view of the device shown in FIG. 8, following application of an anchor cap.

Referring to FIGS. 8-10, there is disclosed a further embodiment of the steering device in accordance with the present invention. The steering device 76 comprises a main body 77 having a proximal wire guide 80, a wire anchor 84 and a pivot region 86. Preferably, the wire guide 80, pivot 86 and anchor 84 are integrally formed from a single extrusion or molded part.

In accordance with a preferred embodiment of the invention, the main body 77 has a maximum diameter of as small as about 0.009 inches or smaller, and is substantially circular in outer cross-sectional configuration, except for a plurality of axially extending channels 85 for receiving guidewires 88 therethrough. Each of the channels 85 preferably has a depth of approximately 0.002 inches, so that 0.0015-inch diameter stainless steel wire can slidably extend therethrough. Channels 85 can conveniently be formed in the extrusion process as axial recesses of the type illustrated in FIGS. 8-10, or by providing parallel sets of radially outwardly extending flanges which extend axially to create a channel 85 therebetween.

Pivot 86 may be formed in any of a variety of ways, which will be apparent to one of skill in the art, and which will depend upon the construction material utilized. For example, in the case of a thermoplastic polymeric extrusion, the pivot region 86 preferably comprises a radially inwardly extending annular depression, which may be formed by application of heat and pressure or by stretching following the extrusion process. Alternatively, the pivot region 86 can be provided by producing an annular recess through other operations such as by physically milling or cutting portions of the extrusion away, or, wire guide 80 and anchor 84 can be secured to a length of metal or polymeric wire, spaced axially apart to provide a flexible length of wire therebetween.

Preferably, the steering device 76 is provided with a deflection wire 88 at each of the four 90° positions around the periphery thereof. (See FIG. 9.) As has been previously discussed, this can be accomplished by providing four separate guidewires which are anchored at the distal end of the steering device 76. However, four deflection wires 88 are effectively provided by assembling the steering device 76 with two continuous deflection wires 88, which loop over the distal end of wire anchor 84 and extend back in a proximal direction as has been discussed.

In assembling the embodiment of the steering device 76 illustrated in FIGS. 8-10, the deflection wires 88 are preferably crossed over the distal end of an extruded main body 77, axially aligned with the free ends extending in the proximal direction. The distal end of the wire anchor 84 is thereafter dipped in or dabbed with an appropriate adhesive, such as an epoxy, to form a cap 90 for securing the deflection wires 88 to the wire anchor 84.

A tubular sleeve 82, such as a length of heat-shrink tubing, is thereafter passed over the distal end of wire anchor 84 and advanced proximally into alignment with the proximal wire guide 80 in a manner which captures each wire 88 within the respective channel 85. Upon application of heat, the annular sleeve 82 reduces in diameter to snugly adhere to the proximal wire guide 80. It has been found that the use of channels 81, having a depth of approximately 0.002 inches, leaves a sufficient tolerance after heat shrinking of sleeve 82 so that stainless steel wires having a diameter of approximately 0.0015 inches can freely axially move therethrough.

The steering assembly is thereafter inserted into a standard guidewire coil 78, and advanced until the proximal wire guide 80 is approximately aligned with the distal end of the flexible steering region of the coil 78. The radial outside surface of the annular sleeve 82 may thereafter be secured to the adjacent coil loops of coil 78, such as by the application of an epoxy or other adhesive 79, as has previously been described.

As will be apparent to one of skill in the art, axial movement of any given deflection wire 88 in a proximal direction will cause the wire 88 to slide through the channel 81 in proximal wire guide 80, and, because the wire 88 is immovably secured to the wire anchor 84, pivot region 86 will flex to permit lateral displacement of wire anchor 84 in the direction of the wire 88 which has been proximally displaced. In this manner, as has been described, the steering device 76 permits selective lateral displacement of the distal tip in any direction, and restoration of the position of the distal end of the steering device back into axial alignment with the axis of the adjacent portion of the guidewire or catheter.

In a modified version (not illustrated) of the device illustrated in FIGS. 8–10, the pivot region 86 is deleted so that the assembled device has an anchor region 84 and a wire guide 80 axially spaced apart and secured to the coils of guidewire body 78. Thus, no post appears in this embodiment. In this embodiment, the deflection wires extend distally from the wire guide 80 toward the anchor 84 as before, but instead of extending substantially parallel to the axis of the steering device 76 as illustrated in FIGS. 8 and 10, each deflection wire crosses the axis of the steering device to the opposite side thereof. Thus, for example, one deflection wire 70 extends through wire guide 80 at the 90° position, then distally at an incline relative to the axis of the steering device to the 180° position on the anchor 84. The wire 70 thereafter in the preferred embodiment loops around the distal end of anchor 84 and extends proximally through the channel 85 at the 90° position thereof. Wire 70 thereafter extends diagonally across the axis of the steering device, through the wire guide 80 at the 180° position, and proximally to the steering control.

As a further alternative, the distal ends of the deflection wires (which may be the midpoint of a long, doubled back wire as previously discussed) are brazed directly to the wire coils of the guidewire body. A brazed joint is most conveniently accomplished on the outside surface of the guidewire body, and the deflection wires preferably extend radially outwardly between adjacent loops on the guidewire body for this purpose. In the case of two deflection wires formed from a single length of wire looping around the steering region of the guidewire, the deflection wire is conveniently looped around the outside of the guidewire body to provide a site for brazing. When a brazed joint is used, the distal wire anchor 84 can be deleted.

Figure 12:
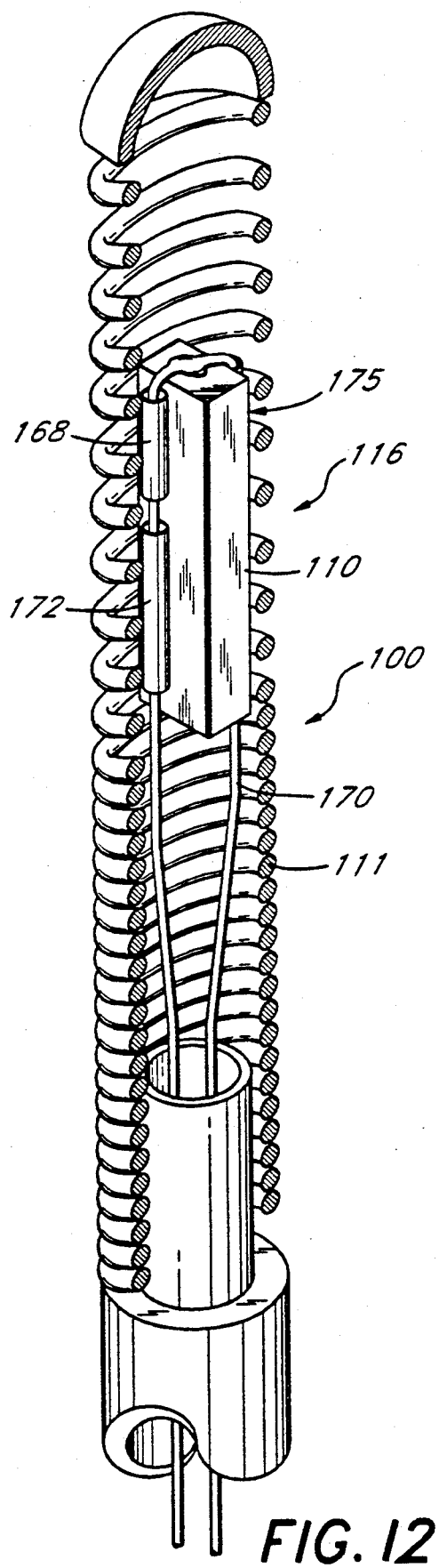
FIG. 12 is a partial sectional perspective view of a simplified steering device according to the present invention, with the outer tubular casing removed.
Figure 13:
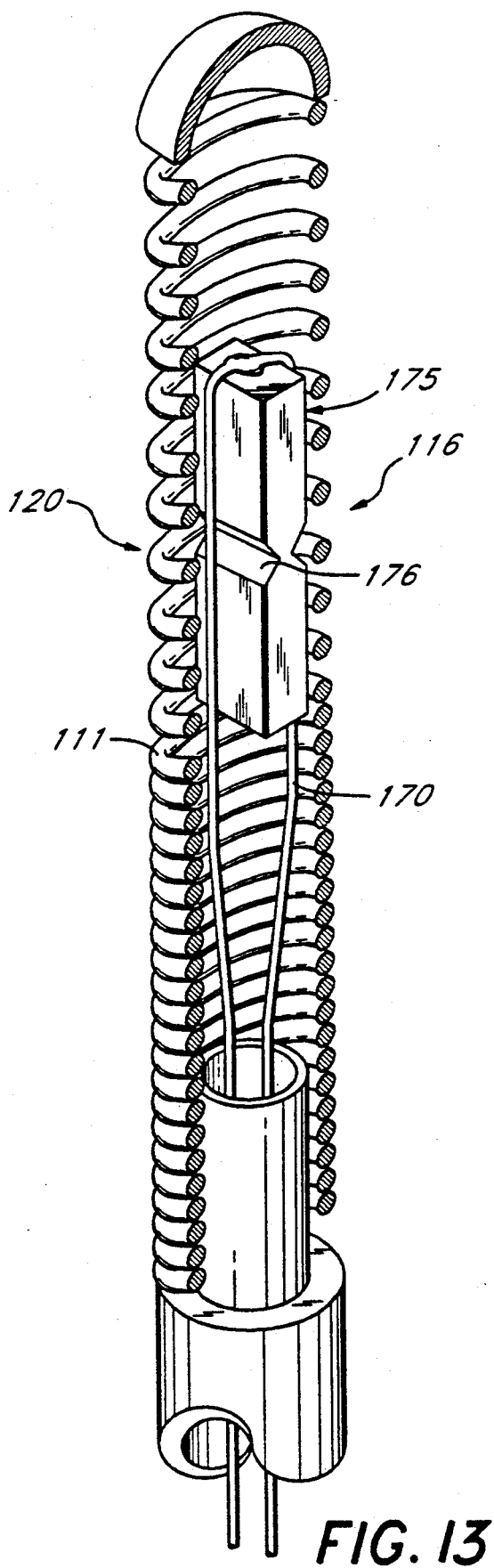
FIG. 13 is an elevational perspective view of a another embodiment of a simplified steering device according to the present invention.

Referring now to FIGS. 12 and 13, there is shown in FIG. 12 a partial sectional perspective view of a two-wire steering device 100 with the outer tubular casing removed. FIG. 13 shows a partial elevational perspective view of a another embodiment of a two-wire steering device 120 according to the present invention. The tubular outer body 111 of the simplified steering devices 100, 120 can be similar to that of any of the various embodiments previously described.

In the simplified steering devices 100, 120 shown, there is provided a flexible steering ribbon 110 disposed within the central lumen of the steering region 116 of the tubular outer body. As will be discussed, "flexible" can mean either a ribbon which can be physically bent or flexed in use, or a more rigid structure provided with a narrowing thereon to form a hinge. In this embodiment, rather than complete 360° steerability, controlled steerability within a single plane is achieved. The improvement over the prior art is that the steering region of the device, once controllably bent, can be restraightened by applying a positive traction to one of the deflection wires.

The steering ribbon 110 may be molded, milled or extruded of any of a variety of known flexible materials, such as spring steel, nylon or other plastic materials. Preferably, the material will permit sufficient lateral flexibility while also exhibiting sufficient axial compressive strength to optimize transfer of axial force into lateral deflection. In a preferred embodiment, ribbon 110 is constructed of nylon.

The steering ribbon 110, as shown, is preferably of substantially rectangular cross-section. However, different cross-sections and dimensions may also prove suitable. Preferably, any cross section which promotes flexibility in a single plane may be provided.

For example, flexibility in a single plane can be facilitated by an appropriate pinching or narrowing of the ribbon 110 such as that sometimes referred to as a "living hinge". See FIG. 13. This type of hinge may be formed in a ribbon 110 of any cross-sectional configuration, by molding, pinching, milling or stretching operations to form a narrowing having a greater propensity to bend than other portions of the ribbon 110. Preferably, the hinge is formed by pinching in a ribbon 110 having a rectangular cross section, however, any cross-sectional configuration may be used so long as flexibility in a single plane is encouraged and the ribbon 110 has sufficient rigidity and strength to withstand the forces applied in multiple flexings and straightenings needed in steering the body 111.

At least one deflection wire 170 is secured with respect to the ribbon 110. In a preferred embodiment, there are two deflection wires 170, one on each of two opposing sides of the ribbon 110 with the distal most portions of the deflection wires (which may be the midpoint of a continuous, doubled back wire as previously discussed) secured with respect to the steering ribbon 110 such as by brazing directly to the steering ribbon. A brazed joint may be accomplished as previously described.

Referring to FIG. 13, a hinge 175 is provided along the ribbon 110 which provides a predicted bending point along the ribbon 110 when the deflection wires 170 are displaced. In the embodiment shown by FIG. 12, the hinge is effectively provided by an axial space between a wire guide 172 and anchor 168 which can be similar to those described in connection with the embodiment illustrated in FIG. 7. In a preferred embodiment there is one guide 172 and one anchor 168 on each side of the ribbon 110 for each of two deflection wires 170. The two guides 172 and anchors 168 are disposed opposite each other to provide the hinge 175 as the space therebetween. The guides 172 and anchors 168 function to secure the wires to the steering ribbon as described in connection with FIG. 7 for securing the wires 70 to the steering post. The length, diameter, positioning, construction and assembly of the guides 172 and anchors 168 will be readily understood by one of skill in the art by reference to the drawings and description above in connection with FIG. 7.

In the embodiment shown in FIG. 13, the hinge 175 is provided by an indentation 176 within the ribbon 110. This form of hinge is known as a living hinge due to the tendency of the hinge to return to its original position. Other forms of living hinges may also be provided. For example, the hinge 175 can be produced by providing a cut out portion in the ribbon, or can be provided by any known method of providing a hinge. Alternatively, the inherent flexibility of the ribbon may be used without the provision of a hinge. See FIG. 12.

In another embodiment of the simplified steering device 100, the steering ribbon 110 may be replaced with two or more substantially parallel ribbons.

In use, the steering device 100 or 120 can be steered in either of two directly opposite steering directions by displacing one of the deflection wires 170. By axial displacement of either of the two deflection wires, a range of motion of the tip of the device is achieved within a circular arc within a plane lying on the longitudinal axis of the steering device 100, 120.

After the device is introduced into the vasculature or other branched system, and a branch or a turn is encountered, in order to enter the branch or turn, the device can be rotated (torqued) to align one of the two steering directions with the branch or turn to be entered. The device can be steered by axial displacement of one of the deflection wires. Advantageously, after the device has been steered toward one direction, the device can be easily straightened by displacing the deflection wire opposing the side toward which the device was steered. The device can then be further advanced through the vasculature.

It must be pointed out that the devices of the present invention can readily be modified by one of skill in the art to allow lateral displacement in only a single direction instead of two opposing directions. For example, the groove in a living hinge type device can be provided on only a single side of the steering ribbon, or other means for stopping or resisting flexing in one direction can be employed as will be readily apparent to one of skill in the art.

An advantage of the simplified steering devices 100, 120 of the present invention is that they can be operated in a manner similar to that employed on convention steering devices for coronary angioplasty and other medical procedures. Thus, one skilled in the art of the prior art procedures could learn to manipulate the steering device of the present invention with little or no additional training.

Although this invention has been described in terms of certain preferred embodiments, other embodiments that are apparent to those of ordinary skill in the art are also within the scope of this invention. Accordingly, the scope of the invention is intended to be defined only by reference to the appended claims.

We claim:

1. A steerable guidewire for percutaneous transluminal insertion into the coronary vascular system and controlled negotiation of branches and turns therein to guide an angioplasty catheter to an arterial stenosis or other treatment site, said guidewire comprising:

an elongate flexible housing having a proximal and a distal end and at least one lumen extending therethrough;

a flexible steering ribbon secured within the lumen, and adapted to displace the distal end of the housing in a lateral direction;

at least one deflection wire guide disposed on the steering ribbon;

at least one deflection wire anchor disposed on the steering ribbon distally of the wire guide; and at least two deflection wires axially movably disposed within the lumen of the flexible housing and extending from a distal point of attachment to the wire anchor throughout the length of the flexible shaft to the proximal end thereof;

wherein axial movement of one of said deflection wires in a proximal direction displaces the axis of a portion of the housing in a lateral direction and axial movement of the other of said deflection wires in a proximal direction returns the axis of a portion of the housing to its original, undisplaced position.

2. A steering device for controlling a flexible steering region on the distal end of an elongate implement, comprising:

a steering ribbon positioned within the steering region of said elongate implement;

at least two deflection wire guides having proximal and distal ends positioned on each of at least two sides of said steering ribbon;

at least two deflection wires secured relative to the steering ribbon and extending proximally adjacent the deflection wire guide;

wherein axial proximal displacement of a first of said two deflection wires causes the steering region to be displaced laterally such as to negotiate a branch or turn in an artery and axial proximal displacement of the second of said two deflection wires causes the laterally displaced steering region to substantially straighten out again.

3. A steering device as in claim 2, wherein the elongate implement comprises a flexible catheter.

4. A steering device as in claim 2 wherein the elongate implement comprises a flexible guidewire.

5. A steering device as in claim 2, wherein said steering ribbon is of rectangular cross section.

6. A steerable guidewire for percutaneous transluminal insertion into the coronary vascular system and controlled negotiation of branches and turns therein to guide an angioplasty catheter to an arterial stenosis or other treatment site, said guidewire comprising:

an elongate flexible shaft having a proximal and a distal end and at least one lumen extending therethrough;

a flexible steering ribbon secured within the lumen, and adapted to displace the distal end of the housing in a lateral direction;

a hinge on the steering ribbon to provide a predicted flexing point along the ribbon; and at least two deflection wires secured to the ribbon;

wherein movement of the first of the two deflection wires in a proximal direction along the housing deflects the distal end from a first position to a second position and movement of the second of the two deflection wires in a proximal direction deflects the distal end from the second position back to the first position.

7. A steerable guidewire as in claim 6, wherein said at least two deflection wires are spaced directly opposite each other with respect to the steering ribbon so that selective proximal movement of the deflection wires will result in a range of motion of said tip within a plane which includes the axis of the flexible shaft.

8. A steerable guidewire as in claim 6, wherein said hinge comprises a living hinge.

9. A steerable guidewire as in claim 6, wherein said hinge comprises an indentation in said steering ribbon.

10. A steerable guidewire as in claim 8, wherein said hinge comprises a cut out portion in the steering ribbon.

11. A steerable implement as in claim 6, wherein said hinge comprises a space between two axially separate components disposed on said ribbon.

12. A steerable implement as in claim 11, wherein said components comprise a steering guide and anchor.

13. A steerable implement, comprising:
   an elongate flexible housing having proximal and distal ends and a central lumen extending therebetween, the distal end of the housing being flexible in a lateral direction;
   an axially extending steering ribbon secured in the housing, and adapted to displace the distal end of the housing in a lateral direction, said steering ribbon having a hinge thereon for allowing motion in either of two directly opposite directions;
   at least two deflection wires having proximal and distal ends extending along the housing, said wires being secured to the steering ribbon; and
   a control at the proximal end of the housing for engaging the proximal ends of the deflection wires to enable said deflection wires to be displaced axially, in relation to said implement;
   wherein the axis of at least a portion of the steering ribbon is displaced laterally in one of the directions of movement of said hinge in response to axial displacement of the first of said deflection wires, thereby causing the distal end of said housing to bend out of the line of the housing longitudinal axis, and the axis of the displaced portion of the steering ribbon is returned to its original position by axial displacement of the second of the deflection wires.

14. A steerable implement as in claim 13, comprising two deflection wires.

15. The implement of claim 13, further comprising a flexible tip attached to the distal end of the housing.

16. A steerable implement as in claim 13, wherein the cross-sectional area of the steering ribbon at the hinge is less than the cross-sectional area of the steering ribbon adjacent to the hinge.

17. A method of steering a guidewire through branches and turns in the coronary vascular system, said guidewire of the type having at least two deflection wires for steering said guidewire and an elongate flexible shaft with a proximal and a distal end, said distal end being provided with a tip which is deflectable out of alignment with the adjacent portion of guidewire to negotiate a turn and then back into substantial alignment with the adjacent portion of guidewire, said method comprising:
   introducing said guidewire into the coronary vascular system;
   advancing said guidewire through the coronary vascular system until a turn is encountered;
   rotating said guidewire until said turn is aligned with a direction in which said tip is deflectable;
   steering said tip of said guidewire into said turn by axial displacement of a first of said deflection wires to deflect the tip out of alignment with the adjacent portion of guidewire and in the direction of the turn;
   advancing said guidewire through said turn; and thereafter
   substantially straightening said guidewire by axial displacement of the second of said deflection wires.

18. A steerable guidewire for percutaneous transluminal insertion into the coronary vascular system and controlled negotiation of branches and turns therein to guide an angioplasty catheter to an arterial stenosis or other treatment site, said guidewire comprising:
   an elongate flexible housing having aproximal and a distal end and at least one lumen extending therethrough;
   a flexible steering ribbon secured within the lumen, and adapted to displace the distal end of the housing in a lateral direction;
   at least two deflection wires axially movably disposed within the lumen of the flexible housing and extending from a distal point of attachment to the steering ribbon throughout the length of the flexible shaft to the proximal end thereof; and
   wherein axial movement of one of said deflection wires in a proximal direction displaces the axis of a portion of the housing in a lateral direction and axial movement of the other of said deflection wires in a proximal direction returns the axis of a portion of the housing to its original, undisplaced position.

19. A steerable guidewire as in claim 18, further comprising a hinge on the steering ribbon.

20. A steerable guidewire as in claim 19, wherein the hinge comprises a region of reduced rigidity in the steering ribbon.

21. A steerable guidewire as in claim 19, wherein the cross-sectional area of the steering ribbon at the hinge is less than the cross-sectional area of the steering ribbon adjacent to the hinge.

* * * * *